United States Patent [19]

Krenning et al.

[11] Patent Number: 6,123,916
[45] Date of Patent: Sep. 26, 2000

[54] THERAPEUTIC USE OF SOMATOSTATIN PEPTIDES

[75] Inventors: Eric Paul Krenning; Steven Willem Jan Lamberts, both of Rotterdam, Netherlands

[73] Assignee: Novartis AG, Basel, Switzerland

[21] Appl. No.: 08/259,090

[22] Filed: Jun. 13, 1994

Related U.S. Application Data

[63] Continuation of application No. 08/109,297, Aug. 19, 1993, abandoned, which is a continuation of application No. 07/659,202, Feb. 21, 1991, abandoned.

[30] Foreign Application Priority Data

Feb. 22, 1990 [GB] United Kingdom .................. 9004017

[51] Int. Cl.⁷ .......................... A61K 51/00; A61K 38/12; A61K 38/31
[52] U.S. Cl. ...................... 424/1.69; 424/1.11; 424/1.41; 514/11; 514/14; 514/15; 514/16; 530/311; 530/317; 930/160
[58] Field of Search ...................................... 530/311, 317; 930/160; 424/1.41, 1.11, 1.69, DIG. 706; 514/11, 14, 15, 16

[56] References Cited

U.S. PATENT DOCUMENTS

| Re. 30,548 | 3/1981 | Vale, Jr. et al. | 525/54.11 |
|---|---|---|---|
| 4,725,577 | 2/1988 | Schalley et al. | 514/11 |
| 4,812,554 | 3/1989 | Riggs et al. | 530/311 |
| 4,853,371 | 8/1989 | Coy et al. | 514/12 |
| 5,225,180 | 7/1993 | Dean et al. | 530/311 |
| 5,382,654 | 1/1995 | Lyle et al. | 530/311 |
| 5,384,113 | 1/1995 | Deutsch et al. | 424/1.69 |

FOREIGN PATENT DOCUMENTS

| 0187622 | 7/1986 | European Pat. Off. | C07K 7/00 |
|---|---|---|---|
| 2206352 | 1/1989 | United Kingdom | A61K 37/02 |
| 2225579 | 6/1990 | United Kingdom | C07K 7/26 |
| 8901476 | 2/1989 | WIPO | C07D 257/02 |

OTHER PUBLICATIONS

Moi et al, Analytical Biochem. 148:249–253 (1985).
Cai et al, PNAS USA 83:1896–1900 (1986).
Krenning et al (1989) The Lancet 1:242–245.
Brechbiel et al (1986) Inorg. Chem. 25:2772–2781.
Reubi et al (1987) J. Clin. Endocrin. Metabolism 65(6):1127–34.
Bakker et al (1990) J. Nucl. Med. 31:1501–1509.
Bakker et al (1991) Life Sciences 49:1583–1591.
Bakker et al. (1991) Life Sciences 49:1593–1601.

*Primary Examiner*—Ponnathapu Achutamurthy
*Assistant Examiner*—Manjunath N. Rao
*Attorney, Agent, or Firm*—Hesna J. Pfeiffer

[57] ABSTRACT

The invention relates to a new pharmaceutical use of somatostatin peptides comprising on the terminal amino group a polyamino polycarboxylic group, in free form or in a pharmaceutically acceptable salt form, particularly in the manufacture of a medicament for treating disorders with an aetiology comprising or associated with excess of GH-secretion.

23 Claims, No Drawings

THERAPEUTIC USE OF SOMATOSTATIN PEPTIDES

This is a continuation of application Ser. No. 08/109,297, filed Aug. 19, 1993, which in turn is a continuation of application Ser. No. 07/659,202, filed Feb. 21, 1991, both of which are abandoned.

The present invention relates to a new use, in particular a new pharmaceutical use, for the compound group comprising somatostatin peptides modified by polyaminopolycarboxylic radicals, in free form or in pharmaceutically acceptable salt form, said compound group being referred to hereinafter collectively as COMPOUNDS OF THE INVENTION.

Accordingly, the COMPOUNDS OF THE INVENTION are somatostatin peptides which comprise on the terminal amino group a polyaminopolycarboxylic group attached to said amino group by an amide bond. Thus, the COMPOUNDS OF THE INVENTION comprise at least one polyaminopolycarboxylic group and further functional groups providing the capability of binding to SRIF receptors.

The term somatostatin peptides includes the naturally occurring somatostatin (tetradecapeptide) and its analogues or derivatives.

By derivatives or analogues as used herein is meant any straight-chain or cyclic polypeptide derived from that of the naturally occurring tetradecapeptide somatostatin wherein one or more amino acid units have been omitted and/or replaced by one or more other amino radical(s) and/or wherein one or more functional groups have been replaced by one or more other functional groups and/or one or more groups have been replaced by one or several other isosteric groups. In general, the term covers all modified derivatives of a biologically active peptide which exhibit a qualitatively similar effect to that of the unmodified somatostatin peptide, e.g. they bind to somatostatin receptors and inhibit pituitary hormone secretion.

Cyclic, bridge cyclic and straight-chain somatostatin analogues are known compounds. Such compounds and their preparation are described e.g. in European Patent Specifications EP-A-1295; 29,579; 215,171; 203,031; 214, 872; 298,732; 277,419.

Preferred COMPOUNDS OF THE INVENTION are those derived from the following somatostatin analogues:

Analogues of the formula I

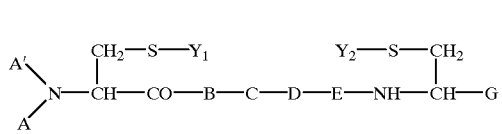

wherein

A is $C_{1-12}$alkyl, $C_{7-10}$phenylalkyl or a group of formula RCO—, whereby
  i) R is hydrogen, $C_{1-11}$alkyl, phenyl or $C_{7-10}$-phenylalkyl, or
  ii) RCO— is
    a) an L- or D-phenylalanine residue optionally ring-substituted by F, Cl, Br, $NO_2$, $NH_2$, OH, $C_{1-3}$alkyl and/or $C_{1-3}$alkoxy;
    b) the residue of a natural or synthetic α-amino acid other than defined under a) above or of a corresponding D-amino acid, or
    c) a dipeptide residue in which the individual amino acid residues are the same or different and are selected from those defined under a) and/or b) above, A' is hydrogen, $C_{1-12}$alkyl or $C_{7-10}$phenylalkyl, $Y_1$ and $Y_2$ represent together a direct bond or each of $Y_1$ and $Y_2$ is independently hydrogen or a radical of formulae (1) to (5)

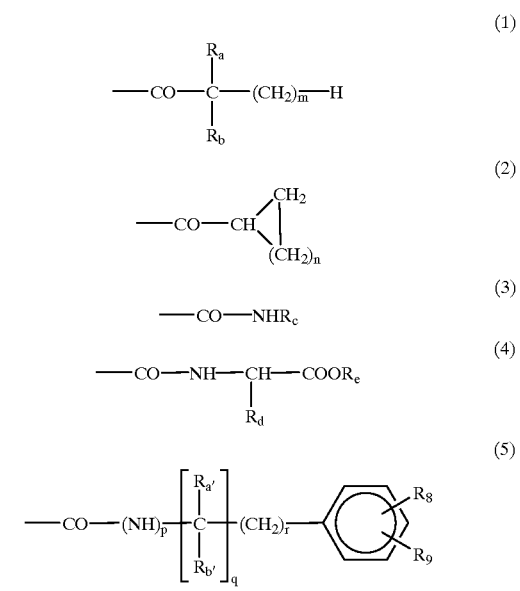

wherein $R_a$ is methyl or ethyl $R_b$ is hydrogen, methyl or ethyl m is a whole number from 1 to 4 n is a whole number from 1 to 5

$R_c$ is $(C_{1-6})$alkyl $R_d$ represents the substituent attached to the α-carbon atom of a natural or synthetic α-amino acid (including hydrogen)

$R_e$ is $(C_{1-5})$alkyl $R_a'$ and $R_b'$ are independently hydrogen, methyl or ethyl, $R_8$ and $R_9$ are independently hydrogen, halogen, $(C_{1-3})$alkyl or $(C_{1-3})$alkoxy, p is 0 or 1, q is 0 or 1, and r is 0, 1 or 2, B is -Phe- optionally ring-substituted by halogen, $NO_2$, $NH_2$, OH, $C_{1-3}$alkyl and/or $C_{1-3}$alkoxy (including pentafluoroalanine), or β-naphthyl-Ala C is (L)-Trp- or (D)-Trp- optionally αN-methylated and optionally benzene-ring-substituted by halogen, $NO_2$, $NH_2$, OH, $C_{1-3}$alkyl and/or $C_{1-3}$ alkoxy, D is Lys, Lys in which the side chain contains 0 or S in β-position, γF-Lys or δ-Lys, optionally α-N-methylated, or a 4-aminocyclohexylAla or 4-aminocyclohexylGly residue E is Thr, Ser, Val, Phe, Ile or an aminoisobutyric or aminobutyric acid residue G is a group of formula

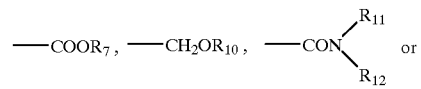

-continued

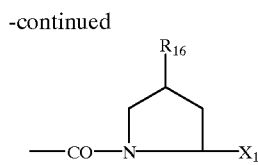

wherein
$R_7$ is hydrogen or $C_{1-3}$alkyl,
$R_{10}$ is hydrogen or the residue of a physiologically acceptable, physiologically hydrolysable ester,
$R_{11}$ is hydrogen, $C_{1-3}$alkyl, phenyl or $C_{7-10}$phenyl-alkyl,
$R_{12}$ is hydrogen, $C_{1-3}$alkyl or a group of formula —CH$(R_{13})$—X$_1$,
$R_{13}$ is CH$_2$OH, —(CH$_2$)$_2$—OH, —(CH$_2$)$_3$—OH, or —CH(CH$_3$)OH or represents the substituent attached to the α-carbon atom of a natural or synthetic α-amino acid (including hydrogen) and
$X_1$ is a group of formula —COOR$_7$, —CH$_2$OR$_{10}$ or —CONR$_{14}$R$_{15}$
wherein
$R_7$ and $R_{10}$ have the meanings given above,
$R_{14}$ is hydrogen or $C_{1-3}$alkyl and
$R_{15}$ is hydrogen, $C_{1-3}$alkyl, phenyl or $C_{7-10}$phenyl-alkyl, and
$R_{16}$ is hydrogen or hydroxy,
with the provisos that when $R_{12}$ is —CH($R_{13}$)—X$_1$ then $R_{11}$ is hydrogen or methyl, and A and A' being so selected that the compound contains a terminal —NH— capable of being linked to a polyaminopolycarboxylic group,
wherein the residues B, D and E have the L-configuration, and the residues in the 2-and 7-position and any residues $Y_1$ 4) and $Y_2$ 4) each independently have the (L)- or (D)-configuration.

B. Analogues of formula II

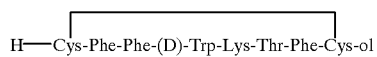

[see Vale et al., Metabolism, 27, Supp. 1, 139, (1978)]

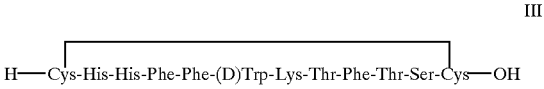

(see EP-A-200,188)

The contents of all the above publications including the specific compounds are specifically incorportated herein by reference.

In the compounds of formula I, the following significances are preferred either individually or in any combination or sub-combination:

1. A is $C_{7-10}$ phenylalkyl, especially phenethyl, or a group of formula RCO. Preferably A is a group of formula RCO.

1.1. Preferably R is $C_{1-11}$ alkyl or $C_{7-10}$ phenylalkyl, especially $C_{7-10}$ phenylalkyl, more especially phenethyl, or RCO has the meanings a), b) or c).

1.2. When RCO has the meaning a) this is preferably a') an L- or D-phenylalanine or -tyrosine residue. More preferably a') is an L- or D-phenylalanine residue.

1.3. When RCO has the meaning b) or c) the defined residue is preferably lipophilic. Preferred residues b) are thus b') α-amino acid residues having a hydrocarbon side chain, e.g. alkyl with 3, preferably 4, or more C atoms, e.g.

up to 7 C-atoms, naphthyl-methyl or heteroaryl, e.g. 3-(2- or 1-naphthyl)-alanine, pyridyl-methyl or tryptophane residue, said residues having the L- or D-configuration, and preferred residues c) are dipeptide residues in which the individual amino acid residues are the same or different and are selected from those defined under a') and b') above.

Example of a residue c) is e.g. 3-(2-naphthyl)-alanine residue.

1.4. Most preferably RCO has the meaning a) especially the meaning a').

2. B is B', where B' is Phe or Tyr.
3. C is C', where C' is (D)Trp.
4. D is D', where D' is Lys, MeLys or Lys(ε-Me), especially Lys.
5. E is E', where E' is Val or Thr, especially Thr.
6. F is F', where F' is a group of formula

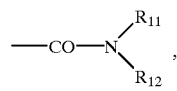

especially a group of formula

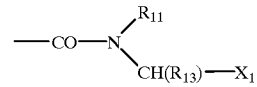

(in which case $R_{11}$=H or CH$_3$). In the latter case the moiety —CH($R_{13}$)—X$_1$ preferably has the L-configuration.

6.1. $R_{11}$ is preferably hydrogen.

6.2. As the substituent attached to the α-carbon atom of a natural amino acid (i.e. of formula H$_2$N—CH($R_{13}$)—COOH), $R_{13}$ is preferably —CH$_2$OH, —CH(CH$_3$)—OH, —(CH$_2$)$_2$—OH, —(CH$_2$)$_3$—OH, isobutyl, butyl, benzyl or 3-indolyl-methyl. It is especially —CH$_2$OH or —CH(CH$_3$)OH.

6.3. $X_1$ is preferably a group of formula

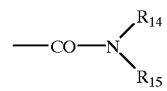

or —CH$_2$—OR$_{10}$, especially of formula —CH$_2$—OR$_{10}$ and $R_{10}$ is preferably hydrogen or has the meaning given under 7 below. Most preferably $R_{10}$ is hydrogen.

The following individual compounds are illustrative of compounds of formula I:

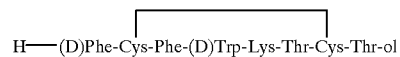

also known as octreotide

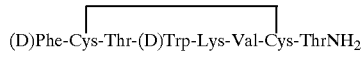

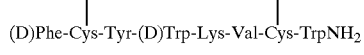

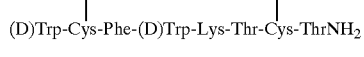

-continued

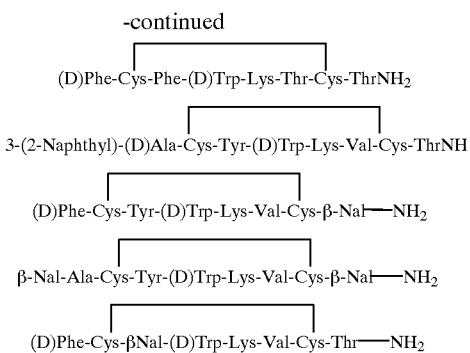

Suitable polyaminopolycarboxylic groups include e.g. those derived from non cyclic ligands e.g. ethylene diamine-tetraacetic acid (EDTA) and diethylene triamine pentaacetic acid (DTPA), as well as macrocyclic ligands, e.g. 1,4,7,10-tetra-azacyclododecane-N,-N',N",N'"-tetraacetic acid (DOTA) or 1,4,8,11-tetraazacyclotetradecane-N,N',N",N'"-tetraacetic acid (TETA). DTPA is preferred.

The COMPOUNDS OF THE INVENTION may exist e.g. in free or salt form. Salts include acid addition salts with e.g. organic acids, polymeric acids or inorganic acids, for example hydrochlorides and acetates, and salt forms obtainable with the carboxylic acid groups present in the molecule, e.g. alkali metal salts such as sodium or potassium, or substituted or unsubstituted ammonium salts.

Preferred COMPOUNDS OF THE INVENTION for use in accordance with the present invention are e.g. compounds of formula Ia As described in GB-A-2,225,579 COMPOUNDS OF THE INVENTION in labelled form have been found to be useful as an imaging agent of tumors or as a therapeutic agent for treating tumors, particularly somatostatin receptor positive tumors.

In accordance with the present invention it has now surprisingly been found that COMPOUNDS OF THE INVENTION exhibit valuable pharmacological properties and are therefore indicated for therapy.

In accordance with the particular findings of the present invention, there is provided in a first aspect:

1. A method of treating disorders with an aetiology comprising or associated with excess of GH-secretion in a subject in need of such a treatment, which comprises administering to said subject an effective amount of a COMPOUND OF THE INVENTION.

In a series of specific or alternative embodiments, the present invention also provides:

1.1. A method of treating diabetes mellitus, and complications thereof or acromegaly in a subject in need thereof, which method comprises administering to said subject an effective amount of a COMPOUND OF THE INVENTION.

Complications of diabetes mellitus are e.g. nephropathy, angiopathy, proliferative retinopathy and dawn phenomenon. The COMPOUNDS OF THE INVENTION are indicated for preventing as well as treating nephropathy, angiopathy and proliferative retinopathy.

In a series of further specific or alternative embodiments, the present invention provides:

2. A method of treating gastro-intestinal disorders in a subject in need thereof, which method comprises administering to said subject an effective amount of a COMPOUND OF THE INVENTION.

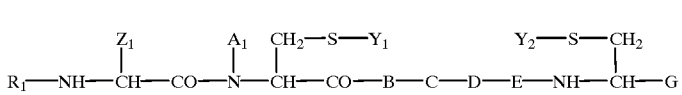

Ia wherein
B, C, D, E, G $Y_1$ and $Y_2$ are as defined above,
$A_1$ is hydrogen or $C_{1-3}$alkyl,
$R_1$ is a diethylene triamine pentaacetic radical (DTPA), and
>N—CH($Z_1$)—CO— is an amino-acid residue such as defined above under a) or b), $Z_1$ being the residue attached in α of such an amino-acid residue,
in free form or in pharmaceutically acceptable salt form.

The polyaminopolycarboxylic group may be attached either directly or indirectly, e.g. by means of a spacer group, to the amino group of the somatostatin peptide. Suitable spacers are e.g. a —NH—$R_x$—CO— group wherein $R_x$ is the residue attached in α to an α-amino-acid.

COMPOUNDS OF THE INVENTION are known. They are disclosed e.g. in UK Patent Publication No 2,225,579 A, the contents thereof relating to said COMPOUNDS being incorporated herein by reference.

Particularly preferred is

Examples of such disorders include e.g. peptic ulcers, entero-cutaneous and pancreaticocutaneous fistulae, irritable bowel syndrom, dumping syndrom, watery diarrhea syndrom, gastro-intestinal bleeding, acute pancreatitis and gastro-intestinal hormone secreting tumours, for example vipomas, glucagonomas, insulinomas, carcinoids, etc.

3. A method of inhibiting proliferation and/or keratinisation of epidermal cells, in a subject in need thereof, which method comprises administering to said subject an effective amount of a COMPOUND OF THE INVENTION.

4. A method of treating degenerative senile dementia in a subject in need thereof, which method comprises administering to said subject an effective amount of a COMPOUND OF THE INVENTION.

5. A method of treating cancer tumours in a subject in need thereof, which method comprises administering to said subject an effective amount of a COMPOUND OF THE INVENTION.

THE COMPOUNDS OF THE INVENTION are particularly indicated for the treatment of somatostatin receptor

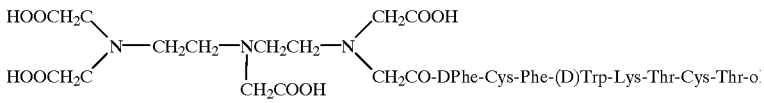

positive tumors, e.g. cancers of the breast, prostate, colon, pancreas, brain, lung and lymph nodes.

As alternatives to the above the present invention also provides:

A. A COMPOUND OF THE INVENTION for use in any method as defined under 1 to 5 above; or B. A COMPOUND OF THE INVENTION for use in the manufacture of a medicament for use in any method as defined under 1 to 5 above; or C. A pharmaceutical composition for use in any method as defined under 1 to 5 above comprising a COMPOUND OF THE INVENTION together with one or more pharmaeutically acceptable diluents or carriers therefor.

Utility of COMPOUNDS OF THE INVENTION in treating diseases and conditions as hereinabove specified, may be demonstrated in standard pharmacological test methods, for example in accordance with the methods hereinafter described.

1. Inhibition of Growth Hormone

The COMPOUNDS OF THE INVENTION reduce GH-release as indicated e.g. by depression of serum GH-levels in rat.

This test is carried out employing male rats. The testsubstance is administered at varying, logarithmically staggered doses employing at least 5 rats per dose. 1 hour after s.c. administration of the test substance blood is taken. The determination of the blood serum GH-level is effected by radio-immuno-assay. The COMPOUNDS OF THE INVENTION are active in this test when administered at a dosage in the range of from 0.02 to 100 µg/kg s.c.

In this test it has for example been determined that

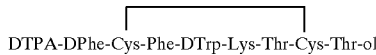
DTPA-DPhe-Cys-Phe-DTrp-Lys-Thr-Cys-Thr-ol has an $ID_{50}$ of 1.29 µg/kg compared with the $ID_{50}$ for natural somatostatin in the same test of 950 µg/kg (the $ID_{50}$ indicates the amount of compound required to lower the GH content by 50% compared with that of untreated control animals).

Furthermore, the GH-reducing activity of the COMPOUNDS OF THE INVENTION was also examined after oral application to male rats with estradiol implants. This test is carried out as follows:

A loop (length 50 mm Θ 3 mm) of silastic with 50 mg of oestradiol is implanted under the dorsal skin of anaesthetized male OFA rats which have a weight of ca. 300 g. At various times (1 to 6 months later), these animals, in a fasted state, are used repeatedly for tests. The test substances are active in this test at doses from 10 to 5000 µg/kg, when GH level in the blood serum is determined by radio-immunoassay 1 and 2 hours after oral administration.

In this test it has for example been determined that

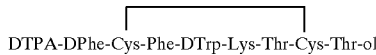
DTPA-DPhe-Cys-Phe-DTrp-Lys-Thr-Cys-Thr-ol has an $ID_{50}$ of 8 µg/kg one hour after oral administration compared with the $ID_{50}$ for Octreotide in the same test of 0.420 mg/kg.

2. Inhibition of gastric- and exocrine and endocrine pancreatic secretion and of the release of various peptides of the gastrointestinal tract These inhibitions can be shown using standard tests, e.g. rats with gastric or pancreatic fistulae. For example, the compounds to be tested are administered to fasted rats with fistula implanted in their stomach by stomach tube. After 1 hour the fistula is opened. The stomach juice is collected in 30 minute periods. The collected volumes are registered and the acid concentration determined. In these tests, the COMPOUNDS OF THE INVENTION are active orally at doses from 0.01 to 10 mg/kg.

3. Anti-Cancer Activity

The COMPOUNDS OF THE INVENTION are effective in the treatment of varous kinds of tumors, particularly the somatostatin receptor positive tumors, as indicated in proliferation tests with various different cancer cell lines and in tumor growth experiments in nude mice with hormone dependent tumors (e.g. gastric dependent colon or pancreas cancer).

The COMPOUNDS OF THE INVENTION possess affinity for somatostatin receptors expressed or overexpressed by tumors and metastases, as visualized by autoradiography on biopsy tissues in standard in vitro binding assays.

A somatostatin receptor positive tumor originating from the human gastro intestinal tract is removed from a patient and immediately put on ice and within a maximal delay of 30 min frozen at −80° C. For further autoradiography this frozen material is cut on a cryostat (Leitz 1720) in 10 µm sections, mounted on precleaned microscope slides and stored at −20° C. for at least 3 days to improve adhesion of the tissue to the slide. The sections are preincubated in Tris-HCl buffer (50 mM, pH 7.4), containing $CaCl_2$ (2mM) and KCl (5mM), for 10 min at ambient temperature and then washed twice for 2 min in the same buffer without additional salts added. The sections are then incubated with

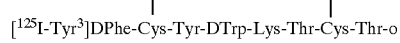
[$^{125}$I-Tyr$^3$]DPhe-Cys-Tyr-DTrp-Lys-Thr-Cys-Thr-o and increasing concentrations of a COMPOUND OF THE INVENTION for 2 hours at ambient temperature in Tris-HCl buffer (170 mM, pH 7.4), containing bovine serum albumin (10 g/l), bacitracin (40 mg/l) and $MgCl_2$ (5 mM) to inhibit endogenous proteases. Incubated sections are washed twice for 5 min in cold incubation buffer containing 0.25 g/l BSA. After a brief dip in distilled water to remove excess salts, the sections are dried quickly and apposed to [$^3$H]-LKB films. It is observed that the COMPOUNDS OF THE INVENTION have a substantial binding affinity to somatostatin receptors. Thus, for

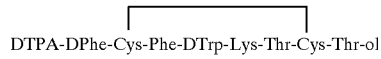
DTPA-DPhe-Cys-Phe-DTrp-Lys-Thr-Cys-Thr-ol a binding affinity of $PK_d$=8.68 nM has been measured.

The utility of the COMPOUNDS OF THE INVENTION is also confirmed in clinical trials.

For all the above indications, the appropriate dosage form will, of course, vary depending upon, for example, the COMPOUND OF THE INVENTION employed, the host, the mode of administration and the nature and severity of the condition being treated. However, in general, satisfactory results in animals are indicated to be obtained at daily dosages from about 0.5 to about 300 µg/kg animal body weight. In larger mammals, for example humans, an indicated daily dosage is in the range from about 2 µg to about 20 mg of a COMPOUND OF THE INVENTION, conveniently in divided doses or in sustained release form. Suitable unit dosage forms contain, for example from about 0.5 µg to about 10 mg of a COMPOUND OF THE INVENTION.

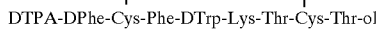

is preferred. For this compound an indicated dose is from 0.02 to 0.4 mg.

In practicing the methods of the present invention, the COMPOUNDS OF THE INVENTION may be administered for example enterally, preferably orally, e.g. in the form of tablets or capsules or parenterally, e.g. in the form of injectable solutions or suspensions.

COMPOUNDS OF THE INVENTION are well tolerated at dosages required for use in accordance with the present invention.

Pharmaceutically acceptable salt forms exhibit the same or similar levels of tolerability/activity as the compounds in free form.

In accordance with a further embodiment of the present invention it has also been found that COMPOUNDS OF THE INVENTION labeled with a γ- or positron-emitting radionuclide are useful radioactive imaging agents for detecting conditions such as e.g. tuberculosis, sarcoidosis, malignant lymphoma, e.g. Hodgkin's disease and non-Hodgkin's disease, Merkel cell tumor of the skin, osteosarcoma, chondrosarcoma, focal lymphocytic reaction, localized autoimmune disease and organ rejection after transplantation (graft versus host rejection).

Accordingly there is provided:

6. A method for in vivo detection of the conditions such as disclosed above in a subject which comprises a) administering a COMPOUND OF THE INVENTION labeled with a γ- or positron-emitting radionuclide to said subject and b) recording the localisation of the receptors targeted by said labeled COMPOUND.

Suitable γ-emitting radionuclides include those which are useful in diagnostic techniques. The γ-emitting radionuclides advantageously have a half-life of from 1 hour to 40 days, preferably from 5 hours to 4 days, more preferably from 12 hours to 3 days. Examples are radionuclides derived from Gallium, Indium, Technetium, Ytterbium, Rhenium and Thallium e.g. $^{67}$Ga, $^{111}$In, $^{99m}$Tc, $^{169}$Yb and $^{186}$Re. Preferably the γ-radionuclide is selected depending on the metabolism of the selected COMPOUND OF THE INVENTION or the somatostatin peptide used. More preferably the COMPOUND OF THE INVENTION is labeled with a γ-radionuclide having a longer half-life than the half-life of the corresponding somatostatin peptide.

Further radionuclides suitable for use in imaging are positron-emitting radionuclides, e.g. $^{68}$Ga.

The biodistribution of the y-labeled COMPOUNDS OF THE INVENTION e.g. in rats can be shown for example in the following test:

Rats bearing transplantable exocrine pancreatic somatostatin receptor positive tumors are treated with an intravenous injection of a COMPOUND OF THE INVENTION labeled with a γ-emitting radionuclide, e.g. $^{111}$In labeled

Injection site is the penis vein. Immediately after administration, the animals are positioned on the collimator of a gamma-camera and the distribution of radioactivity is monitored at various time intervals.

Biodistribution of radioactivity may also be determined through serial sacrifice of a number of such treated rats and determination of the organ radioactivity.

After administration of a COMPOUND OF THE INVENTION labeled with a γ-radionuclide, at a dosage of from 1 to 5 μg/kg of COMPOUND labeled with 0.1 to 2 mCi radionuclide the tumor site becomes detectable together with the organs where excretion essentially takes place.

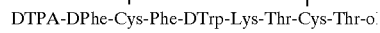

is administered i.v. at a dosage of 4 μg/kg body weight labeled with 0.5 mCi$^{111}$In and the radioactivity is assessed 3 min, 10 min, 20 min, 20 hrs and 48 hrs. 3 minutes after injection, radioactivity is detected in kidneys, urinary bladder and in the tumor site. Radioactivity is increasing and is very intensely localized on the tumor site 20 hrs after injection.

The labeled COMPOUNDS OF THE INVENTION for use as an imaging agent in method (6) may be administered parenterally, preferably intravenously, e.g. in the form of injectable solutions or suspensions, preferably in a single injection. The appropriate dosage will of course vary depending upon, for example, the COMPOUND and the type of detectable element used, e.g. the radionuclide. A suitable dose to be injected is in the range to enable imaging by photoscanning procedures known in the art. It may advantageously be administered in a dose having a radioactivity of from 0.1 to 50 mCi, preferably 0.1 to 30 mCi.

In animals an indicated dosage range may be of from 0.1 to 10 μg/kg of COMPOUND labeled with 0.1 to 2 mCi γ-emitting radionuclide, e.g. $^{111}$In. In larger mammals, for example humans, an indicated dosage range may be of from 1 to 200 μg COMPOUND labeled with 0.1 to 50 mCi, preferably 0.1 to 30 mCi, e.g. 3 to 15 mCi, γ-emitting radionuclide, depending on the γ-emitting radionuclide used. For example with In, it is preferred to use a radioactivity in the lower range, whereas with Tc, it is preferred to use a radioactivity in the upper range.

The enrichment of the targeted sites with the labeled COMPOUNDS may be followed by the corresponding imaging techniques, e.g. using nuclear medicine imaging instrumentation, for example a scanner, γ-camera, rotating γ-camera, each preferably computer assisted; PET-scanner (Positron emission tomography); MRI equipment or CAT scanning equipment.

The COMPOUNDS OF THE INVENTION when labeled with a α- or β-emitting radionuclide exhibit also valuable pharmacological properties and are therefor indicated for therapy.

Suitable β-emitting radionuclides include those which are useful in therapeutic applications, for example $^{90}$Y, $^{67}$-Cu, $^{186}$Re, $^{188}$Re, $^{169}$Er, $^{121}$Sn, $^{127}$Te, $^{143}$Pr, $^{198}$Au, $^{109}$Pd, $^{165}$Dy, $^{32}$p, $^{142}$Pr. The β-radionuclide advantageously have a half-life of from 2.3 hrs to 14.3 d, preferably from 2.3 to 100 hrs. Preferably the β-emitting radionuclide is selected in order to have a longer half-life than the half-life of the COMPOUND used.

Suitable α-emitting radionuclides are those which are used in therapeutic treatments, e.g. $^{211}$At, $^{212}$Bi.

In accordance with the present invention, there is provided in a further embodiement:

7. A method for in vivo treatment of malignant lymphoma, Merkel cell tumor of the skin, osteosarcoma or chondrosarcoma in a subject in need of such a treatment which comprises administering to said subject a therapeutically effective amount of a COMPOUND OF THE INVENTION labeled with a α- or β-emitting radionuclide.

Dosages employed in practising the therapeutic method of the present invention will of course vary depending e.g. on the particular condition to be treated, for exemple the type of the tumor, the particular COMPOUND employed, for exemple the half-life of the labeled COMPOUND in the tumor, and the therapy desired. In general, the dose is calculated on the basis of radioactivity distribution to each organ and on observed target uptake. For example the labeled COMPOUND may be administered at a daily dosage range having a radioactivity of from 0.1 to 3mCi/kg body weight.

In animals an indicated dosage range may be of from 0.1 to 5 µg/kg of COMPOUND labeled with 0.1 to 3 mCi α- or γ-emitting radionuclide, e.g. $^{90}$Y. In larger mammals, for example humans, an indicated daily dosage range is of from 1 to 200 µg COMPOUND labeled with 0.1 to 3 mCi/kg body weight, e.g. 0.1 to 1.5 mCi/kg body weight α- or β-emitting radionuclide, conveniently administered in divided doses up to 4 times a day.

The α- or β-labeled COMPOUNDS OF THE INVENTION may be administered by any conventional route, in particular parenterally, e.g. in the form of injectable solutions or suspensions. They may also be administered advantageously by infusion, e.g. an infusion of 30 to 60 min. Depending on the site of the tumor, they may be administered as close as possible to the tumor site, e.g. by means of a catheter. The mode of administration selected may depend on the dissociation rate of the COMPOUND used and the excretion rate.

The labeled COMPOUNDS OF THE INVENTION may be administered in free form or in pharmaceutically acceptable salt form.

The labeled COMPOUNDS OF THE INVENTION may preferably be prepared shortly before the administration to a subject, i.e. the radio-labeling with the desired detectable metal ion, particularly the desired α-, β- or γ-radionuclide, may be performed shortly before the administration.

According to a further aspect of the invention, there is provided:

D. a pharmaceutical composition for use in any method as defined under 6. and 7., comprising a labeled COMPOUND according to the invention in free or in pharmaceutically acceptable salt form, together with one or more pharmaceutically acceptable carriers or diluents therefor.

Such compositions may be manufactured in conventional manner.

A composition according to the invention may also be presented in separate package with instructions for mixing the COMPOUND with the metal ion and for the administration of the resulting labeled COMPOUND, e.g. in form of a kit.

What is claimed is:

1. A method for treating disorders with an aetiology comprising or associated with excess GH-secretion, for treating gastro-intestinal disorders, for inhibiting proliferation and/or keratinisation of epidermal cells, or for treating degenerative senile dementia in a subject in need of such a treatment, which comprises administering to said subject an effective amount for treating said disorders of a somatostatin peptide modified at the terminal amino group by a polyaminopolycarboxylic group attached to the terminal amino group by an amide bond, in free form or in pharmaceutically acceptable salt form.

2. A method for the in vivo detection of tuberculosis, sarcoidosis, malignant lymphoma, Merkel cell tumor of the skin, osteosarcoma, focal lymphocytic reaction, localized autoimmune disease, and organ rejection after transplantation in a subject in need thereof, which comprises a) administering to said subject a labeled somatostatin peptide modified at the terminal amino group by a polyaminopolycarboxylic group attached to the terminal amino group by an amide bond, in free form or in pharmaceutically acceptable salt form and labeled with a γ- or positron-emitting radionuclide in an amount effective for said in vivo detection and b) recording the localization of the receptors targeted by said labeled somatostatin peptide.

3. A method for treating malignant lymphoma, Merkel cell tumor of the skin, or osteosarcoma in a subject in need of such a treatment which comprises administering to said subject a therapeutically effective amount for said treatment of a labeled somatostatin peptide modified at the terminal amino croup by a polyaminopolycarboxylic group attached to the terminal amino group by an amide bond, in free form or in pharmaceutically acceptable salt form and labeled with a α- or β-emitting radionuclide.

4. A method according to claim 1, wherein the somatostatin peptide is selected from a compound of formula I

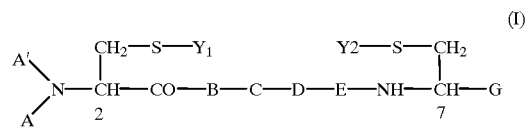

wherein

A is $C_{1-12}$ alkyl, $C_{7-10}$phenylalkyl or a group of the formula RCO—, where i) R is hydrogen, $C_{1-11}$alkyl, phenyl or $C_{7-10}$-phenylalkyl, or ii) RCO— is a) an L- or D-phenylalanine residue optionally ring-substituted by F, Cl, Br, $NO_2$ $NH_2$, OH, $C_{1-3}$alkyl and/or $C_{1-3}$alkoxy;

b) the residue of a natural or synthetic a-amino acid other than defined under a) above or of a corresponding D-amino acid; or c) a dipeptide residue in which the individual amino acid residues are the the same or different and are selected from those defined under a) and/or b) above, A' is hydrogen, $C_{1-12}$alkyl or $C_{7-10}$phenylalkyl, $Y_1$ and $Y_2$ represent together a direct bond or each of $Y_1$ and $Y_2$ is independently hydrogen or a radical of formulae (1) to (5)

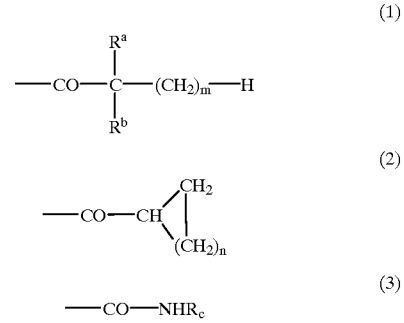

-continued

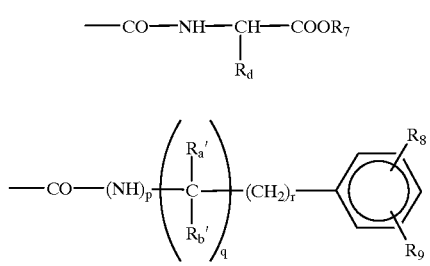

wherein
$R_a$ is methyl or ethyl,
$R_b$ is hydrogen, methyl or ethyl,
m is a whole number from 1 to 4,
n is a whole number from 1 to 5,
$R_c$ is $(C_{1-6})$alkyl,
$R_d$ represents the substituent attached to the α-carbon atom of a natural or synthetic a-amino acid,
$R_e$ is $(C_{1-5})$alkyl,
$R_a'$ and $R_b'$ are independently hydrogen, methyl, or ethyl,
$R_8$ and $R_9$ are independently hydrogen, halogen, $(C_{1-3})$alkyl, or $(C_{1-3})$alkoxy,
p is 0 or 1,
q is 0 or 1, and
r is 0, 1 or 2,
B is —Phe— optionally ring-substituted by halogen, $NO_2$, $NH_2$, OH, $C_{1-3}$alkyl and/or $C_{1-3}$ alkoxy, or β-naphthyl-Ala,
c is (L)-Trp- or (D)-Trp- optionally α-N-methylated and optionally benzene-ring-substituted by halogen, $NO_2$, $NH_2$, OH, $C_{1-3}$alkyl and/or $C_{1-3}$ alkoxy,
D is Lys, Lys in which the side chain contains O or S in the β-position, γ-Lys or δF-Lys, optionally α-N-methylated, or a 4-aminocyclohexylAla or 4-aminocyclohexylGly residue,
E is Thr, Ser, Val, Phe, Ile or an aminoisobutyric or aminobutyric acid residue,
G is a group of the formula —COOR$_7$, —CH$_2$OR$_{10}$, —CONR$_{11}$R$_{12}$ or, —CO—N(R$_{16}$-pyrrolidine)—X$_1$, wherein
$R_7$ is hydrogen or $C_{1-3}$alkyl,
$R_{10}$ is hydrogen or a physiologically acceptable, physiologically acceptable, physiologically hydrolysable ester thereof,
$R_{11}$ is hydrogen, $C_{1-3}$alkyl, phenyl or $C_{7-10}$phenylalkyl,
$R_{12}$ is hydrogen, $C_{1-3}$alkyl or a group of formula —CH(R$_{13}$) —X$_1$,
$R_{13}$ is —CH$_2$OH, —(CH$_2$)$_2$—OH, —(CH$_2$)$_3$—OH, or —CH(CH$_3$)OH or represents the substituent attached to the α-carbon atom of a natural or synthetic a-amino acid, and
$X_1$ is a group of formula —COOR$_7$, —CH$_2$OR$_{10}$ or —CONR$_{14}$R$_{15}$
wherein
$R_7$ and $R_{10}$ have the meanings given above,
$R_{14}$ is hydrogen or $C_{1-3}$alkyl, and
$R_{15}$ is hydrogen, $C_{1-3}$alkyl, phenyl, or $C_{7-10}$ophenylalkyl, and
$R_{16}$ is hydrogen or hydroxy,
with the provisos that when $R_{12}$ is —CH(R$_{13}$)—X$_1$, then $R_{11}$ is hydrogen or methyl, and A and A' being so selected that the compound contains a terminal —NH— capable of being linked to a polyaminopolycarboxylic group,
wherein the residues B, D and E have the L-configuration, and the residues in the 2-and 7-position and any residues $Y_1$ 4) and $Y_2$ 4) each independently have the (L)- or (D)- configuration;
a compound of Formula II

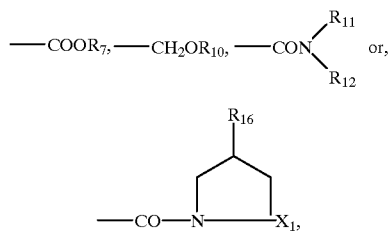

a compound of Formula III

III

H—Cys-His-His-Phe-Phe-(D)Trp-Lys-Thr-Phe-Thr-Ser-Cys—OH.

5. Method according to claim 4, wherein in formula I
A is RCO which is
a) an L- or D-phenylalanine residue optionally ring-substituted by F, Cl, Br, $NO_2$, $NH_2$, OH, $C_{1-3}$alkyl and/or $C_{1-3}$alkoxy;
b) the residue of a natural or synthetic α-amino acid other than defined under a) above or of a corresponding D-amino acid, or
c) a dipeptide residue in which the individual amino acid residues are the same or different and are selected from those defined under a) and/or b) above,
B is Phe or Tyr,
C is (D)Trp,
D is Lys,
E is Val or Thr, and
G is a group of formula —CONR$_{11}$R$_{11}$ wherein $R_{11}$ and $R_{12}$ are as defined in claim 4.
6. Method according to claim 1, wherein the polyaminopoly-carboxylic group is ethylene diaminetetraacetic acid, diethylene triamine pentaacetic acid, 1,4,7,10-tetraaza-cyclododecane-N,N',N'',N'''-tetraacetic acid or 1,4,8,11-tetraazacyclotetradecane-N,N',N'',N'''-tetraacetic acid.
7. A method according to claim 4, wherein the labeled somatostatin peptide modified at the terminal amino group is a compound of formula Ia

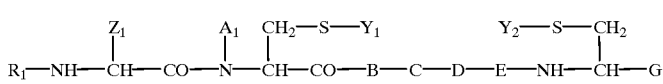

Ia wherein B, C, D, E, G, $Y_1$, and $Y_2$ are as defined in claim 4, $A_1$ is hydrogen or $C_{1-4}$alkyl, and $R_1$ is a diethylene triamine pentaacetic acid residue, and $Z_1$ is the residue attached to the α-carbon of an amino acid residue as defined in a) or b) of claim 4. in free form or in pharmaceutically acceptable salt form.

8. A method according to claim 1, wherein the somatostatin peptide modified at the terminal amino group is

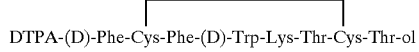

in free form or in pharmaceutically acceptable salt form.

9. A method according to claim 2, wherein the labeled somatostatin peptide modified at the terminal amino group is

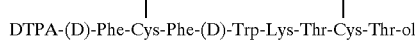

in free form or in pharmaceutically acceptable salt form labeled with a γ- or positron-emitting radionuclide.

10. A method according to claim 2, wherein the γ-emitting radionuclide is selected from $^{67}$Ga, $^{111}$In, $^{99m}$Tc, $^{169}$Yb, and $^{186}$Re.

11. A method according to claim 2, wherein the positron emitting radionuclide is $^{68}$Ga.

12. The method according to claim 2, wherein the labeled somatostatin peptide modified at the terminal amino group is

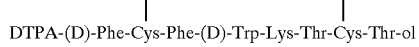

in free form or in pharmaceutically acceptable salt form labeled with $^{111}$In.

13. The method according to claim 2 for the detection of tuberculosis.

14. The method according to claim 2 for the detection of sarcoidosis.

15. The method according to claim 2 for the detection of malignant lymphoma.

16. The method according to claim 2 for the detection of Merkel cell tumor of the skin.

17. The method according to claim 2 for the detection of osteosarcoma.

18. The method according to claim 2 for the detection of focal lymphocytic reaction.

19. The method according to claim 2 for the detection of localized autoimmune disease.

20. The method according to claim 2 for the detection of organ rejection after transplantation.

21. A method according to claim 3, wherein the labeled somatostatin peptide modified at the terminal amino group is

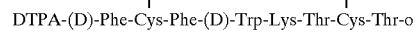

in free form or in pharmaceutically acceptable salt form labeled with a α- or β-emitting radionuclide.

22. A method according to claim 3, wherein the β-emitting radionuclide is selected from $^{90}$Y, $^{67}$Cu, $^{186}$Re, $^{188}$Re, $^{169}$Er, $^{121}$Sn, $^{127}$Te, $^{143}$Pr, $^{198}$Au, $^{109}$Pd, $^{165}$Dy, $^{32}$P, and $^{142}$Pr.

23. A method according to claim 3, wherein the α-emitting radionuclide is selected from $^{211}$At and $^{212}$Bi.

* * * * *